United States Patent [19]

Beaton

[11] 4,124,607

[45] Nov. 7, 1978

[54] PREPARATION OF STEROL SUBSTRATES FOR BIOCONVERSION

[75] Inventor: John M. Beaton, Portage, Mich.

[73] Assignee: The Upjohn Company, Kalamazoo, Mich.

[21] Appl. No.: 787,720

[22] Filed: Apr. 15, 1977

[51] Int. Cl.² ............................................. C07J 9/00
[52] U.S. Cl. ............................................. 260/397.25
[58] Field of Search .................................. 260/397.25

[56] References Cited

U.S. PATENT DOCUMENTS

| | | | |
|---|---|---|---|
| 2,866,797 | 12/1958 | Berry et al. | 260/397.25 |
| 2,963,494 | 12/1960 | Cunningham et al. | 260/397.25 |
| 3,840,570 | 10/1974 | Julian | 260/397.25 |
| 3,879,431 | 4/1975 | Clark et al. | 260/397.25 |

*Primary Examiner*—Elbert L. Roberts
*Attorney, Agent, or Firm*—Bruce Stein

[57] ABSTRACT

This invention relates to a process whereby sterols from various sources are prepared for subsequent fermentation by dissolving the sterols in an organic diluent with subsequent removal of the organic diluent producing high substrate concentrations for fermentation.

20 Claims, No Drawings

PREPARATION OF STEROL SUBSTRATES FOR BIOCONVERSION

BACKGROUND OF THE INVENTION

Various methods of adding fermentable substrates to fermentation media for bioconversion are known to those skilled in the art. The most common of these are adding the fermentable substrate in solution, as a dry powder or a powder in aqueous suspension. These methods usually provide substrate concentrations of about 0.5–20 g./l.

The addition of fermentable substrates to the fermentation medium in an organic water-miscible solvent is well known to those skilled in the art. For example, methanol or acetone may be used, see Tetrahedron 18, 581 (1962) at page 487. Ethyl alcohol has been used to add Reichstein's Compound S for fermentation, see J.A.C.S. 75, 5369 (1953) and Applied Microbiology 3, 16 (1955). Various lower aliphatic acid amides and the N-alkyl derivatives thereof, in particular DMF (N,N-dimethylformamide), have been used to add various steroids to fermentation media, see U.S. Pat. No. 3,138,541 and Applied Microbiology 7, 276 (1959).

In U.S. Pat. No. 3,770,586 the 21-hydroxy steroids are added in the form of a 21-hydrocarbon dicarboxylic acid ester alkali metal salt. This salt has increased water solubility and therefore higher effective substrate concentrations (2–15 g./l.) are obtained.

Alternatively, the fermentable substrate can be added to the aqueous fermentation medium in a powdered form. Progesterone has been added in this manner, see I and EC Process Design and Development 5, 285 (1966). When the progesterone was added in a finely divided particle size obtained by grinding, efficient bioconversions at substrate concentrations of 20–50 g./l. were obtained, see Applied Microbiology 8, 345 (1960). An alternative method of adding a powdered fermentable substrate to fermentation medium is by micronization. Here the substrate (progesterone) is comminuted which allows for efficient bioconversion at substrate concentrations in the range of 16–20 g./l., see U.S. Pat. No. 3,201,324.

U.S. Pat. No. 3,840,570 discloses a process for the preparation of sterols from plant sources, especially tall oil pitch, by extraction with a water-alcohol-hydrocarbon mixture followed by saponification and subsequent purification. A. H. Conner, et al. in Applied and Environmental Microbiology 32, 310 (1976) describe the microbial conversion of tall oil sterols and crude sitosterol from soy beans to androstenedione-type compounds using DMF as the solvent for introducing sterols to the fermentation. The process of the present invention generates a concentrated aqueous suspension of very finely divided or microcrystalline sterols by dissolving sterols from a sterol source in a volatile organic diluent, addition of the solution to an aqueous system, and rapid removal of the organic diluent.

While the most common method utilized for adding fermentable substrates to fermentation media involves dissolving the fermentable substrate in an aqueous miscible organic diluent and adding that diluent to the fermentation medium, this process has the problem that due to the toxicity of the organic diluents to the microorganisms in the fermentation medium, the concentration of the aqueous miscible organic diluent must be kept low. Since the concentration of the aqueous miscible organic diluent must be kept low, the amount of substrate which can be added to the fermentation will of course be limited (usually less than 2 g./l.).

The problem with adding powders to the fermentation medium is that they tend to clump and not disperse well. Sterols tend to be waxy and do not undergo milling very well, hence it is difficult to obtain finely ground powders.

W. C. McGregor et al. Biotechnol, Bioeng. 14, 831 (1972) described a pilot plant bioconversion of a steroid using a resting cell suspension. Several methods of introducing the substrate for bioconversion were attempted including adding the steroid dissolved in methylene chloride. The present invention differs from the McGregor process in that (1) the sterol or sterols in an organic diluent are added to an aqueous system prior to inoculation with the microorganism and (2) the organic diluent is removed producing very finely divided or microcrystalline sterols. Additionally, McGregor et al. indicate that adding the steroid in methylene chloride was not very satisfactory, see page 835, while the method of the present invention produces excellent results.

S. I. Ladinskaya et al. in Gidroliz. Lesokhim Prom. 24, 7 (1971) and O. I. Andreeva et al. ibid, 24, 28 (1971) disclose methods of obtaining crystalline phytosterols from a sterol-ethanol solution by addition of water. An alcohol-water suspension of crystals is totally unsuitable for fermentation. The present invention produces an aqueous suspension of very finely divided or microcrystalline sterols which is suitable for fermentation.

The process of the present invention is a method for adding a sterol or sterols to an aqueous system for bioconversion which differs from prior processes in that the material to be fermented is added to the aqueous system in an organic diluent which is removed from the aqueous system by heat and/or reduced pressure. Upon removal of the organic diluent an aqueous suspension of very finely divided or microcrystalline sterols results which is suitable for fermentation. The present invention permits the addition of large amounts of fermentable substrate to the fermentation medium without the retention of a toxic organic diluent. Additionally, the process of the present invention provides substrate concentration as high as 200 g./l.

Processes for the preparation of a source of sterols for bioconversion have become all the more important now that a process has been developed to cleave the side chain of sterols to produce androsta-1,4-diene-3,17-dione and androst-4-ene-3,17-dione, see U.S. Pat. Nos. 3,684,657 and 3,759,791. Note especially, that the examples in U.S. Pat. No. 3,759,791 show that sterols from various sources may be utilized for conversion to androst-4-ene-3,17-dione and androsta-1,4-diene-3,17-dione.

BRIEF DESCRIPTION OF THE INVENTION

Disclosed is a process for preparing a sterol or sterols for bioconversion which comprises:

(1) dissolving the sterol or sterols in an organic diluent forming a solution;

(2) adding the solution to an aqueous system; and (3) removing the organic diluent.

The definitions and explanations below are for the terms as used throughout the entire patent application including both the specification and the claims.

All temperatures are in degrees Centigrade.

DMF refers to N,N-dimethylformamide.

U.S.P. refers to United States Pharmacopiea.

N.F. refers to National Formulary.

Microcrystalline refers to crystals smaller than 0.02 mm × 0.02 mm × 0.1 mm.

Tween 80 refers to polysorbate 80 as marketed by Atlas Chemical Ind., DuPont Bldg., Wilmington, Delaware, U.S.A.

Triton X-100 ® refers to p-t-octylphenoxynonaethoxyethanol as marketed by Rohm and Haas, Philadelphia, Pennsylvania, U.S.A.

Crude sitosterol is crude soy sterols which have had the stigmasterol content reduced to about 4%. It contains mostly β-sitosterol, campesterol, minor amounts of other sterols, hydrocarbons and fatty alcohols.

Technical sitosterol is obtained by dissolving the crude sitosterol in an organic diluent and crystallizing out approximately 50% of the solids.

Purified sitosterol is Sitosterols NF XIII.

Soy sterols are the sterols which are isolated as a by-product in the refining of soy bean oil.

Rapeseed sterols are the sterols in rapeseed oil.

DETAILED DESCRIPTION OF THE INVENTION

The process of the present invention describes the process for preparing sterols for bioconversion which comprises dissolving the sterols in an organic diluent forming a solution, adding the solution to an aqueous system and removing the organic diluent.

Sterols is a generic term meaning lanosterol and steroidal alcohols with the basic formula:

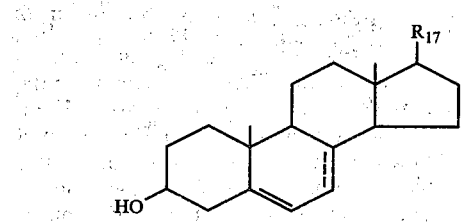

where $R_{17}$ contains 8 thru 10 carbon atoms and where --- is a single or double bond. Examples of some of these sterols are cholesterol, brassicasterol, campesterol, stigmasterol, β-sitosterol, and ergosterol. The side chain at $C_{17}$ may contain unsaturation.

When any of these sterols or sources containing them are subjected to bioconversion by microorganisms which are capable of metabolizing only the $C_{17}$ side chain, the products are mainly androstane derivatives for example, androst-4-ene-3,17-dione. Hence various sterols would be useful substrates for fermentation according to the processes of U.S. Pat. Nos. 3,684,657 and 3,759,791.

Plant sterols (phytosterols), animal sterols (wool grease — cholesterol and lanosterol) and fungal sterols (ergosterol) are a source of substrate. Numerous sources of sterols are therefore available for bioconversion. It is preferred that the sources of sterols contain a sterol selected from the group consisting of stigmasterol, β-sitosterol, campesterol, ergosterol, brassicasterol, cholesterol and lanosterol or mixtures thereof. It is preferred that the source of sterols is selected from the group consisting of soy bean oil, corn oil, rice bran oil, peanut oil, sunflower seed oil, safflower oil, cottonseed oil, rapeseed oil, coffee seed oil, wheat germ oil, tall oil, and wool grease. It is more preferred that the source of sterols be selected from the group consisting of soy bean oil, corn oil, peanut oil, sunflower seed oil, rapeseed oil, tall oil, and wool grease.

It is well known to those skilled in the art that the sources of sterols listed above do contain the varous sterols previously described, see J. Am. Oil Chem. Soc. 50, 122 (1973), ibid, 52, 334 (1975) and Process for Upgrading Hardwood and Softwood Soaps, presented by H. Gronfors and B. Holmbom at AlChE Meeting in Boston, Sept. 7-10, 1975, at page 4.

A source of sterols are the vegetable oils of many plants. The vegetable oils usually contain less than 1% sterols. However, the refining of crude vegetable oils generates by-product streams, some of which are rich in sterols and from which sterols of greater than 50% concentration may be obtained. For example soy bean oil is obtained from soy beans and contains less than 1% sterols, the major sterol being β-sitosterol. Upon the purification (deodorization, etc.) of the soy bean oil to produce an edible grade of soy bean oil the sterols are concentrated and further enriched by crystallization yielding a solid mass containing greater than 60% sterols which is termed soy sterols, soya sterols or soy bean sterols. It is this sterol mixture (soy sterols) which is prepared for bioconversion by the process of the present invention. Likewise, with other sources of sterols (rapeseed oil, tall oil, wool grease, etc.) the crystallized unsaponifiable fractions are suitable to be prepared for bioconversion according to the process of the present invention.

Therefore, with regards to the plant kingdom while the ultimate source of the sterols is the plant or the oil extracted from the vegetable material, the immediate source is the concentrated sterol residue emerging as a by-product from purification of the vegetable oil. The immediate source of sterols to be prepared for bioconversion may be a mixture of sterols from the various sources, previously described.

In the animal kingdom, wool grease (lanosterol and cholesterol) is a source of sterols.

A problem with the use of sterols has been the fact that they are waxy and difficult to prepare for fermentation. The present invention has solved that problem and provides an easy method to prepare sterols for fermentation.

The sterols are dissolved in an organic diluent, with heat if necessary. Examples of the organic diluent include heptane, hexane, pentane, cyclohexane, methylene chloride, ethylene dichloride, chloroform, carbon tetrachloride, acetone, methanol, ethanol, and mixtures of these and other organic diluents. The sterol dissolved in the organic diluent is added to water slowly. The water is heated sufficiently in order to distill off the organic diluent. The temperature to which the water is heated and maintained may vary with the particular organic diluent(s) utilized. The rate of addition of the sterol-organic diluent solution to the water should be controlled so that the organic diluent is distilled off without accumulating appreciably in the aqueous system. This can be achieved by supplying heat to maintain a suitable distillation rate. Alternatively, the organic diluent may be removed by lowering the pressure. Additionally, the organic diluent may be removed by a combination of heating and vacuum. It is preferred the organic diluent be removed by heating, with or without a vacuum. Upon addition of the entire sterol-organic diluent solution to the water and the distillation of the organic diluent the reaction vessel may be flushed with a gas such as nitrogen to remove the last traces of the organic diluent. Removal of the organic diluent by the manner described in the present invention is very advantageous because it allows for recycling of the organic diluent. It is preferred that during the process of the present invention the aqueous system be agitated. In addition various additives such as soy bean oil, polysorbate 80 (Tween ® 80) or p-t-octylphenoxynonaethoxyethanol (Triton X-100) may be added to the organic diluent or the aqueous system prior to or at the time the sterol-organic diluent is added.

Following removal of all organic diluent and flushing by nitrogen, the aqueous suspension of sterols is prepared for fermentation. This includes adding of various nutrients which are necessary for the particular microorganism which is to be utilized in the fermentation. The sterols will provide a source of carbon because the side chain of the sterols will be cleaved and metabolized by the particular microorganism used in the fermentation. Supplementary sources of carbon may also be added. The pH is also adjusted as is appropriate for the particular microorganism to be used in the fermentation. The fermentation mixture is then sterilized by methods well known to those skilled in the art and inoculated with the particular microorganism to be used for the fermentation.

Alternatively, the organic diluent containing the sterols is added to an aqueous mixture already containing some or all of the various additional nutrients needed for the fermentation. Upon distillation of the organic diluent the remainder, if any, of the additional nutrients are added, the pH adjusted if necessary, and then the fermentation-sterol mixture is ready for sterilization and inoculation with the desired microorganism. It is preferred that the aqueous system to which the sterol-organic diluent solution is added be water.

EXAMPLES

The invention may be more fully understood from the following examples which are illustrative of the process of the present invention but are not to be construed as limiting.

Example 1 Crude sitosterol

Crude sitosterol (2.54 kg.) is dissolved in dry heptane:ethylene dichloride [11.8 l., 37:63 (v/v)] at 50°–55°. This mixture is added to agitated water (18.0 l.) heated to 92° at atmospheric pressure at such a rate as to maintain a water temperature of 90°–92° while heating the vessel with steam and collecting the solvent by distillation. When the addition is complete, the vessel is flushed with nitrogen to remove the last traces of the organic diluents. The aqueous slurry is cooled for utilization in a subsequent fermentation. The concentration of sterols is 140.8 g./l. The slurry may be diluted further with water if desired. Nutrients are added, the mixture is sterilized, and inoculated with an appropriate microorganism.

Example 2 Crude sitosterol

Crude sitosterol (200 g.) and polysorbate 80 (0.5 ml.) are dissolved in heptane:ethylene dichloride [700 ml., 37:63 (v/v)] at about 50°. The mixture is added to water (1000 ml.), maintained at 90°–92° with agitation while the organic diluent is collected as an azeotrope with water by distillation. The last traces of the diluents are removed by flushing the hot sterol suspension with nitrogen. The resulting aqueous suspension has a sterol concentration of 179 g./l. After separation of the water from the organic diluents, the distillate may be reused in the same process. The aqueous suspension is cooled, nutrients added, sterilized and inoculated with an appropriate microorganism.

Example 3 Crude sitosterol

Crude sitosterol (200 g.) is dissolved in ethylene dichloride-heptane [1600 ml., 63–37 (v/v)] at 50°–55°. The mixture is sucked into agitated water at 70° under distillation conditions at 0.5 atmospheres. Air is then sucked through the hot slurry to remove the last traces of the organic diluents. The concentration of the sterols in the aqueous suspension is 66 g./l. The aqueous suspension is cooled, nutrients added, sterilized and inoculated with an appropriate microorganism.

Example 4 Technical sitosterol

Technical sitosterol (200 g.) is dissolved in methylene chloride (4 l.) and is added to agitated water (3 l.) at 75° containing Triton X-100 (0.5 ml.) under distillation conditions. Upon removal of the methylene chloride by distillation the last traces of the methylene chloride are removed by flushing with nitrogen to give an aqueous suspension with a sterol concentration of 65 g./l. The aqueous suspension is cooled, nutrients added, sterilized and inoculated with an appropriate microorganism.

Example 5 Purified sitosterol

Purified sitosterol (200 g.) is dissolved in methylene chloride (4 l.) and transferred with slight nitrogen pressure through a syringe needle below the surface of the water (3 l.). The water is kept at 75°. When the addition is complete, nitrogen is blown over the surface of the hot agitated water to remove the last traces of the methylene chloride. Triton X-100 (2 g.) is added. The sterol concentration is 65 g./l. The sterol-water mixture is cooled, nutrients added, sterilized and inoculated with the appropriate microorganism.

Example 6 Purified sitosterol

Purified sitosterol (400 g.) is dissolved in methylene chloride (4 l.). The mixture is added to agitated water (3 l.) containing polysorbate 80 (8.0 ml.) which is maintained at 82° with external heat under distillation conditions. The addition takes approximately 4 hours. After removal of the methylene chloride by distillation, the last traces of the organic diluents are removed by flushing with nitrogen which produces an aqueous suspension with a sterol concentration of 127 g./l. The aqueous suspension is cooled, nutrients added, sterilized and inoculated with an appropriate microorganism.

Example 7 Crude sitosterol — unreacted sterols

A mixture of crude sitosterol (180 g.) and unreacted sterols (20 g.) from a previous fermentation is dissolved in methylene chloride (4 l.) and added to agitated water at 75°. Upon removal of the organic diluent by distillation and flushing with nitrogen an aqueous sterol suspension of 66 g./l. is obtained. The aqueous suspension is cooled, nutrients added, sterilized and inoculated with an appropriate microorganism.

Example 8 Stigmasterol

Stigmasterol (46 g.) is dissolved in warm methylene chloride (920 ml.). The mixture is added at atmospheric pressure to agitated water (690 ml.) at 75° under distillation conditions. The temperature is maintained at 75° by external heat. Upon distillation of the organic diluent and flushing with nitrogen to remove the last traces of the organic diluent an aqueous suspension of stigmasterol is obtained with a concentration of 65 g./l. The aqueous suspension is cooled, nutrients added, sterilized and inoculated with an appropriate microorganism.

Example 9 Cholesterol

Cholesterol USP (100 g.), Triton X-100 (10 ml.) and soy bean oil (5 g.) are dissolved in methylene chloride (2000 ml.). The mixture is added at atmospheric pressure to agitated water (1500 ml.) maintaining a temperature of 75° by steam heat. Upon distillation of the organic diluent and flushing with nitrogen to remove the last traces of the organic diluent, a concentration of cholesterol crystals in the cooled aqueous slurry is 63 g./l. The aqueous suspension is cooled, nutrients added, sterilized and inoculated with an appropriate microorganism.

Example 10 Rapeseed sterols

Rapeseed sterols (46 g.) are dissolved in warm methylene chloride (920 ml.). The mixture is added at atmospheric pressure to agitated water (690 ml.) at 75°–80° under distillation conditions maintaining a water temperature of 75°–80° by external heat. Upon removal of the organic diluent by distillation and flushing with nitrogen to remove the last traces of the organic diluent the concentration of sterols is 71 g./l. The aqueous suspension is cooled, nutrients added, sterilized and inoculated with an appropriate microorganism.

Example 11 Ergosterol

Ergosterol (46 g.) and Triton X-100 (0.10 g.) is dissolved in methylene chloride (3.5 l.). The mixture is added to agitated water (890 ml.) at 75°. Following distillation of the organic diluent the last traces of the organic diluent are flushed out with nitrogen to give an aqueous slurry containing 66 g./l. of ergosterol. The aqueous suspension is cooled, nutrients added, sterilized and inoculated with an appropriate microorganism.

Examples 12–22

Following the procedure of Examples 1–11, respectively, but substituting fermentation media for water a mixture is obtained containing the sterols and nutrients ready to be sterilized.

Example 23 Bioconversion of sterols by the process of U.S. Pat. No. 3,684,657

Following the procedure of Example 1 the aqueous suspension of sterols is diluted to a concentration of 5 g./l. Peptone (0.5%), meat extract (0.3%), and yeast extract (0.1%) are added. The mixture is sterilized by heating 1 hour at 121° followed by cooling to about 30° and then inoculation in the appropriate way with a culture of Mycobacterium sp., NRRL B-3683. The mixture is incubated aerobically at 30°–32° for approximately 1 week producing androst-4-ene-3,17-dione and androsta-1,4-diene-3,17-dione.

Example 24 Bioconversion of sterols by the process of U.S. Pat. No. 3,759,791

Following the procedure of Example 1 the aqueous suspension of sterols is diluted with water to a concentration of 1 g./l. Peptone (0.5%), meat extract (0.3%), yeast extract (0.1%) are added. The mixture is sterilized by heating for 1 hour at 121° followed by cooling to about 30° and then inoculation in the appropriate manner with a culture of Mycobacterium sp., NRRL B-3805. The mixture is incubated aerobically at 30°–32° for approximately 1 week producing androst-4-ene-3,17-dione.

I claim:

1. A process for preparing an aqueous suspension of microcrystalline sterol or sterols for bioconversion which comprises:
   (1) dissolving the sterol or sterols in an organic diluent forming a solution,
   (2) adding the solution to an aqueous system, and
   (3) simultaneously removing the organic diluent.

2. A process according to claim 1 where the sterol or sterols are selected from the group consisting of stigmasterol, β-sitosterol, campesterol, ergosterol, brassicasterol, cholesterol and lanosterol or mixtures thereof.

3. A process according to claim 2 where the sterol is β-sitosterol.

4. A process according to claim 1 where the sterol or sterols are of plant, animal, or fungal origin.

5. A process according to claim 4 where the sterol or sterols is provided by a source of sterols which is selected from the group consisting of soy bean oil, corn oil, rice bran oil, peanut oil, sunflower seed oil, safflower oil, cottonseed oil, rapeseed oil, coffee seed oil, wheat germ oil, tall oil, and wool grease or mixtures thereof.

6. A process according to claim 5 where the source of sterols is selected from the group consisting of soy bean oil, corn oil, peanut oil, sunflower seed oil, rapeseed oil, tall oil, and wool grease.

7. A process according to claim 6 where the source of sterols is soy bean oil.

8. A process according to claim 6 where the source of sterols is corn oil.

9. A process according to claim 6 where the source of sterols is peanut oil.

10. A process according to claim 6 where the source of sterols is sunflower seed oil.

11. A process according to claim 6 where the source of sterols is rapeseed oil.

12. A process according to claim 6 where the source of sterols is tall oil.

13. A process according to claim 6 where the source of sterols is wool grease.

14. A process for preparing an aqueous suspension of microcrystalline sterols from a source of sterols containing β-sitosterol for bioconversion which comprises:
    (1) dissolving the source of sterols containing β-sitosterol in an organic diluent forming a solution,
    (2) adding the solution to an aqueous system, and
    (3) simultaneously removing the organic diluent by heat.

15. A process for preparing an aqueous suspension of microcrystalline soy bean sterols for bioconversion which comprises:
    (1) dissolving the soy bean sterols in an organic diluent forming a solution,
    (2) adding the solution to water, and
    (3) simultaneously removing the organic diluent by heat.

16. A process according to claim 1 where the organic diluent is selected from the group consisting of heptane, hexane, pentane, cyclohexane, methylene chloride, ethylene dichloride, chloroform, carbon tetrachloride, acetone, methanol, ethanol and mixtures thereof.

17. A process according to claim 16 where the organic diluent is a heptane-ethylene dichloride mixture.

18. A process according to claim 16 where the organic diluent is methylene chloride.

19. A process according to claim 1 where the aqueous system is water.

20. A process according to claim 1 where the aqueous system is fermentation medium.

* * * * *